US009107652B2

(12) United States Patent
Ragin et al.

(10) Patent No.: US 9,107,652 B2
(45) Date of Patent: Aug. 18, 2015

(54) SAMPLING DEVICES AND METHODS

(75) Inventors: Yancy Kenan Ragin, Columbia, MD (US); Bert Jungheim, Boyds, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 794 days.

(21) Appl. No.: 12/622,150

(22) Filed: Nov. 19, 2009

(65) Prior Publication Data
US 2011/0118626 A1 May 19, 2011

(51) Int. Cl.
*A61B 10/00* (2006.01)
*A61B 10/02* (2006.01)
*B01L 3/02* (2006.01)
(Continued)

(52) U.S. Cl.
CPC ........... *A61B 10/0291* (2013.01); *B01L 3/0293* (2013.01); *B01L 3/5082* (2013.01); *A61B 10/0096* (2013.01); *A61B 2010/0216* (2013.01); *B01L 2300/0609* (2013.01); *G01N 2001/028* (2013.01)

(58) Field of Classification Search
CPC ............... A61B 10/02; A61B 10/0291; A61B 2010/0216; A61B 10/0096
USPC .......................................... 600/569, 570, 572
See application file for complete search history.

(56) References Cited

U.S. PATENT DOCUMENTS

| 4,108,162 A | 8/1978 | Chikashige et al. |
| 4,803,050 A * | 2/1989 | Mack ............................... 422/65 |

(Continued)

FOREIGN PATENT DOCUMENTS

| DE | 102006049135 | 4/2008 |
| DE | 202009007427 | 11/2009 |

(Continued)

OTHER PUBLICATIONS

International Search Report and Written Opinion for PCT Application No. PCT/US2010/057443 date Jun. 6, 2011.
(Continued)

*Primary Examiner* — Max Hindenburg
*Assistant Examiner* — Jonathan M Foreman
(74) *Attorney, Agent, or Firm* — RatnerPrestia

(57) ABSTRACT

An automated sample aspirating method in which a magnetic force is applied to a collection tube containing a sample carrier to move at least the top of the carrier to a location off the center axis of the collection tube. An aspirator is inserted into the tube at a vertical position along the sample carrier, and a fluid is aspirated from the tube. Also provided are a sample collector having a tip adapted to obtain a sample from a sample source, and a handle that extends from the tip and is magnetic at a location remote from the tip. Also provided is a sample processing system having a sample collector such as described above, a collection tube adapted to hold the sample collector with the tip at a closed lower end of the tube and the handle extending towards an open upper end of the tube, and a cap that seals the sample collector tip and at least a portion of the handle inside the tube. Also provided is a sample processing system having a sample holding rack having at least one opening adapted to hold one or more sample containers, a sample processing device adapted to move along a predetermined path into the one or more sample containers and process a sample contained therein, and one or more magnets adapted to displace an object in the one or more sample containers out of the predetermined path of the sample processing device.

28 Claims, 4 Drawing Sheets

(51) Int. Cl.
  *B01L 3/00*  (2006.01)
  *G01N 1/02*  (2006.01)

(56) References Cited

U.S. PATENT DOCUMENTS

| | | | |
|---|---|---|---|
| 5,128,105 A * | 7/1992 | Berthold et al. | 422/561 |
| 5,183,638 A * | 2/1993 | Wakatake | 422/64 |
| 5,355,544 A | 10/1994 | Dirksing | |
| 5,422,273 A | 6/1995 | Garrison et al. | |
| 5,476,796 A * | 12/1995 | Takahashi et al. | 436/526 |
| 5,571,481 A * | 11/1996 | Powell et al. | 422/562 |
| 6,521,190 B1 | 2/2003 | Edens et al. | |
| 6,790,654 B2 * | 9/2004 | Malinge | 435/299.2 |
| 6,806,094 B2 * | 10/2004 | Anderson et al. | 436/180 |
| 7,182,912 B2 * | 2/2007 | Carey et al. | 422/64 |
| 7,384,600 B2 * | 6/2008 | Burns et al. | 422/64 |
| 7,615,382 B2 | 11/2009 | Wang et al. | |
| 2005/0238540 A1 | 10/2005 | Swon et al. | |
| 2009/0280572 A1 * | 11/2009 | Ribeiro et al. | 436/164 |
| 2010/0159463 A1 * | 6/2010 | Eder et al. | 435/6 |
| 2011/0177592 A1 * | 7/2011 | Faustman et al. | 435/325 |

FOREIGN PATENT DOCUMENTS

| | | |
|---|---|---|
| WO | WO 2009/024559 | 2/2009 |
| WO | WO 2010/062546 | 6/2010 |

OTHER PUBLICATIONS

European Search Report for Application No. 10832265.2 dated Sep. 12, 2014.

* cited by examiner

SAMPLING DEVICES AND METHODS

BACKGROUND

1. Field of the Art

The present application describes various inventions relating to medical sampling systems, such as an automated system for moving sample brushes to facilitate sample aspiration, and features and methods associated with the same. Uses outside the medical field are also possible.

2. Description of Related Art

A number of medical sampling processes use a sample brush, swab, or similar sample carrier device to obtain a sample from a patient. Once a sample is obtained, the brush or other sampling tool may be stored in a tube or other vessel with a sealed top until the sample is tested. For example, tests for the Human Papilloma Virus ("HPV") often employ a cytology brush that is used to collect cells from the cervical area. After the sample is collected, the end of the cytology brush on which the sample resides is broken from the remainder of the brush at a pre-existing score line, then sealed in a collection tube. The collection tube typically includes a solution in which the sample is preserved, which may be introduced into the tube before or after the brush and sample are placed in the tube. The HPV sample tube, with the brush included, is then sent to a laboratory to test for the presence of HPV genetic material.

Sampling systems in which the brush or other sampling device is stored in the sample vessel, such as the foregoing HPV test, provide certain benefits. For example, it is not necessary for the clinician to extract the sample from the sampling tool before it is placed in the vessel, and the sample is more likely to remain uncontaminated from the time it is taken until the time it is tested. In addition, the amount of biological waste at the clinician's work site may be reduced by at least some degree.

Despite their many advantages, it has been found that sampling systems in which the sampling device is stored along with the sample in a vessel can cause complications or inconveniences when it comes time to process the sample for testing. For example, it may be desirable to aspirate the sample from the vessel without removing the brush. This may be desirable to simplify the testing process, avoid unnecessary spills, and reduce the number of separate biological waste items. In addition, cells or other media being tested may be removed along with the brush, thereby diluting the sample quality. While it is desirable to keep the brush in the vessel as the sample is aspirated, it has been discovered that the brush or other tool may create a significant impediment to sample aspiration, particularly where it is desired to automate the aspiration process. For example, it has been found that an automated pipetting device can contact an HPV sample carrier in a significant number of aspiration attempts, leading, in some instances, to improper or inadequate aspiration. Given the desirability of providing accurate and timely test results of large numbers of samples, this problem has been an impediment to developing automated assaying and testing systems.

In view of the foregoing, it has been determined that there is a need for alternative systems and methods for medical sampling and testing. Further, while the following discussion emphasizes uses in particular areas of the medical field, it will be readily apparent that the inventions described herein may be used separately or together, and may have medical and testing applications beyond those described herein and even outside the medical field.

SUMMARY

The present disclosure provides a number of inventions that may be used collectively, in various combinations, or alone. The following summary provided examples of such inventions, and does not limit the invention as claimed in any way.

In one exemplary aspect, there is provided an automated sample aspirating method. the method may include providing a collection tube having a sample carrier located therein, applying a magnetic force to move at least a top end of the sample carrier to a location off a center axis of the collection tube, inserting an aspirator into the collection tube at a vertical position adjacent at least a portion of the sample carrier, and aspirating a fluid from the collection tube through the aspirator.

In another exemplary aspect, there is provided a sample collector having a tip adapted to obtain a sample from a sample source, such as a human patient, and a handle extending from the tip. The handle is magnetic at a location remote from the tip.

In another exemplary aspect, there is provided a sample processing system having a sample collector, a collection tube, and a cap. The sample collector has a tip adapted to obtain a sample from a sample source and a handle extending from the tip. The handle is magnetic at a location remote from the tip. The collection tube has a closed lower end and an open upper end, and is configured and dimensioned to hold the sample collector with the tip at the closed lower end and the handle extending towards the open upper end. The cap is configured and dimensioned to seal the open upper end of the collection tube with the sample collector tip and at least a portion of the sample collector handle inside the collection tube.

In another exemplary aspect, there is provided a sample processing system having a sample holding rack, a sample processing device, and one or more magnets. The sample holding rack has at least one opening adapted to hold one or more sample containers. The sample processing device, such as a pipette aspirator, is adapted to move along a predetermined path into the one or more sample containers and process a sample contained therein. The one or more magnets, which may be mounted on the rack, on the processing device, or elsewhere on the system, are adapted to displace an object in the one or more sample containers out of the predetermined path of the sample processing device.

DETAILED DESCRIPTION OF EXEMPLARY EMBODIMENTS

The embodiments described below generally relate to a process and system in which a sample carrier, such as a brush or swab, is used to collect a sample, the brush and sample are placed in a collection tube, and the sample is aspirated from the tube using an automated system. Examples of automated systems and other devices with which exemplary embodiments of the invention may be used are disclosed in U.S. application Ser. No. 12/588,304 filed on Oct. 9, 2009, U.S. application Ser. No. 12/622,131 entitled "Multiple-Input Analytical System" filed on Nov. 19, 2009, and U.S. application Ser. No. 12/622,140 entitled "Sample Vial Retainer" filed on Nov. 19, 2009. The foregoing applications are incorporated herein by reference in their entireties.

As noted above, a problem with such systems is that a pipette used to aspirate the sample can contact the brush, potentially leading to sampling problems. To address this problem, the brush includes a metallic member, and the sampling system uses a magnet to pull the brush out of likely contact with the pipette or other aspirating device. Such a system is subject to a host of variations, and the descriptions herein are not intended to be all-inclusive or otherwise limit the scope of the invention. Furthermore, while the present disclosure provides systems that work collectively to obtain a desired result, the various aspects of these systems may be used separately, as desired, and constitute separate inventive aspects of the disclosure. Still further, while the embodiments described herein are applicable to the medical field, they also may find applicability in various other fields, and are not intended to be limited to medical applications.

Figure 1:
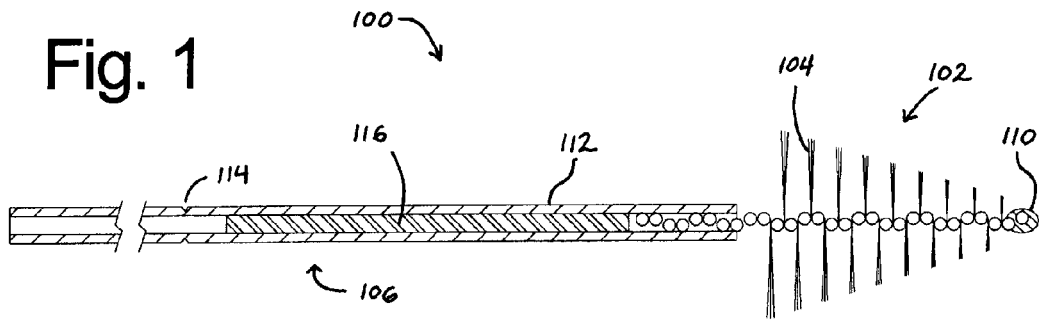
FIG. 1 is a cross-sectional side view of a first exemplary embodiment of a sampling brush according to one aspect of the invention.

Referring to FIG. 1, in a first exemplary embodiment, there is provided a sample carrier 100 that may be used in medical procedures or in other processes. This first exemplary carrier 100 has a tip 102 with a bristle 104, and a handle 106 extending from the tip 102. The tip 102 may comprise any structure suitable for gathering a sample, such as a brush, a cotton swab, or a simple flat scraper. In the exemplary embodiment, the tip 102 is formed by twisted wires 108 that hold the fibers that form the bristle 104 and give the bristle 104 a generally helical shape. The end of the wires 108 may have a protective cover 110 of epoxy or other material to inhibit the wires from injuring the patient or damaging tissue or other substances being sampled. The bristle 104 may have a typical conical cervical brush shape, such as shown, but it may alternatively have any other suitable shape as may be desirable for the intended use. Any suitable synthetic or natural fibers may be used to form the bristle 104, as known in the art.

The handle 106 extends from the carrier tip 102 and is configured and dimensioned to permit the user to maneuver the bristle 104 to obtain a sample. The handle 106 may comprise a simple straight shaft, but it may be bent or angled to aid in the sampling process. As shown, the handle 106 may have a hollow shaft 112 formed of any suitable material, such as glass, plastic, metal, or the like. The shaft 112 is attached to the tip 102 by locating a portion of the twisted wires 108 inside the handle 106. Any suitable method may be used to attach the shaft 112 to the tip 102. For example, the handle 106 may be molded in place over the wires 108 to secure them in place, or the wires 108 may be friction fit in the handle 106, secured by adhesives, or secured by any other suitable method to the handle. In other embodiments, the shaft 112 need not be hollow, and it may form the backbone of the tip portion of the carrier 100. For example, the shaft may be a solid plastic or wooden rod that has bristles or a cotton swab adhered to the end.

In some cases, the handle 106 may be longer than a sample container (described below) in which the carrier 100 is stored after sampling. To account for this, the handle 106 may be scored by notches 114 or have circumferential grooves, cuts, perforations, or other features creating a weak point at which the handle 106 can be easily and accurately broken to fit the tip 102 and a short length of the handle 106 into the sample container. Such notches 114 or the like may be formed in any way, such as by cutting, pressing or molding them into the shaft 112.

The handle 106 of the carrier 100 is magnetic. As used herein, "magnetic" means having a substantial ability to be attracted by a magnet or otherwise moved by a magnetic field. Something that is "magnetic" may have a magnetic field of its own, but this is not required. In this embodiment, the handle 106 is provided with magnetic properties by including a magnetic insert 116 inside the hollow shaft 112. The magnetic insert 116 may comprise a suitable magnetic material, such as a strip or wire of alloy 430 stainless steel. The insert 116 preferably is located where it does not extend to any notches 114 or other features provided as a break point along the shaft 112. The insert 116 may be magnetic, but does not necessarily have its own substantial persistent magnetic field. The magnetic insert 116 may be held in place by a friction fit, adhesives, being molded in place, or by any other suitable methods or means. It is preferred, but not required in all embodiments, for the sample carrier 100 to be biocompatible with cervical cell sample collection processes and methods. Locating the magnetic insert 116 inside the hollow shaft 112 provides a benefit by shielding the insert 116 from the sample and any fluid medium or reagents that may be included in the collection tube. This may reduce the likelihood of contact and reaction between the insert 116 and the sample or other media, which could contaminate the sample or create testing errors.

Figure 2:
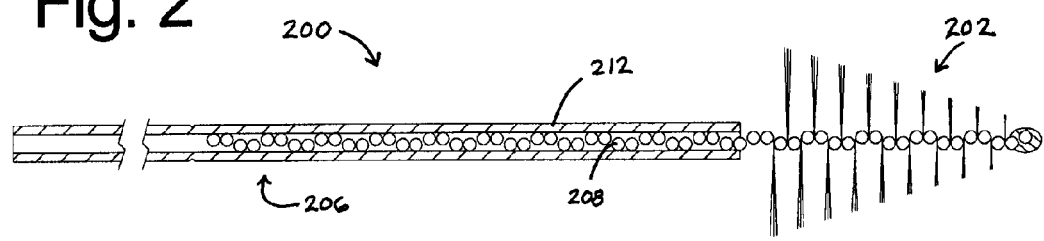
FIG. 2 is a cross-sectional side view of a second exemplary embodiment of a sampling brush according to another aspect of the invention.

Another exemplary embodiment is shown in FIG. 2. In this embodiment, a carrier 200 is provided having a typical cervical brush configuration with a bristled tip 202 formed on a twisted wire 208, and a handle 206 comprising a hollow plastic shaft 212. In this embodiment, the twisted wire 208 has been extended significantly further into the hollow shaft 212 than is typically necessary to simply secure the tip 202 to the shaft 206, so that the wire 208 is located substantially along the entire length of the portion of the carrier 200 that is broken off and retained in the collection tube. In this embodiment, the wire 208 itself forms a magnetic insert. If necessary, the entire wire or the portion of the wire that extends outside the shaft 212 may be coated or otherwise treated to prevent or inhibit reaction with samples, media or reagents in the collection tube.

In addition to the foregoing exemplary embodiments, other embodiments and configurations of carriers having magnetic handles are also envisioned. For example, instead of providing a separate magnetic insert or extending the bristle wire into the handle, the handle itself may be formed from a magnetic material such as steel. In other embodiments, a magnetic part may be attached to the outside of the handle. In such embodiments the magnetic part may comprise, for example, a metal ring, sleeve or hose that is slipped over the handle and secured in place. Magnetic material also may be applied in the form of a film, a sprayed deposit, particles adhered to the handle, a wire wrapped around the handle, and so on. Depending on the nature of the sample and storage media and the testing reagents being used, a configuration in which the magnetic part is potentially exposed to the contents of the collection tube may require coatings or other features to prevent contact and reactions between the handle and the sample or other media.

Sample carriers according to embodiments of the invention may be produced using any suitable system, method or means. For example, carriers including a separate insert or an extended twisted wire insert may be manufactured in a production facility, sterilized, and provided separately or with suitable collection tubes for distribution as kits. Alternatively, pre-existing sample carriers, such as existing cervical brushes, may be modified by either the clinician or the testing laboratory to make the carrier handle magnetic. For example, before the sample carrier is placed in the collection tube, a magnetic ring or sleeve may be slipped over the end of the handle, a magnetic clip may be attached to the handle, or a magnetic wire or pin may be installed inside the handle if it is hollow.

As noted above, 430-series Stainless Steel may be preferred in one embodiment to provide magnetic properties to the carrier handle. However, any other suitable magnetic material may be used to make the handle magnetic. For example, other metals or alloys may be used, provided the material does react with and contaminate the sample, or is shielded from the sample in some way to prevent such contamination. Also, some non-metallic and plastic materials exhibit magnetic properties, and to the extent they have suitable properties, they may be used in other embodiments of the invention. Such plastic magnetic materials may provide an effective alternative arrangement in which the handle itself is formed as the magnetic material, and a separate magnetic part is not required.

Figure 3:
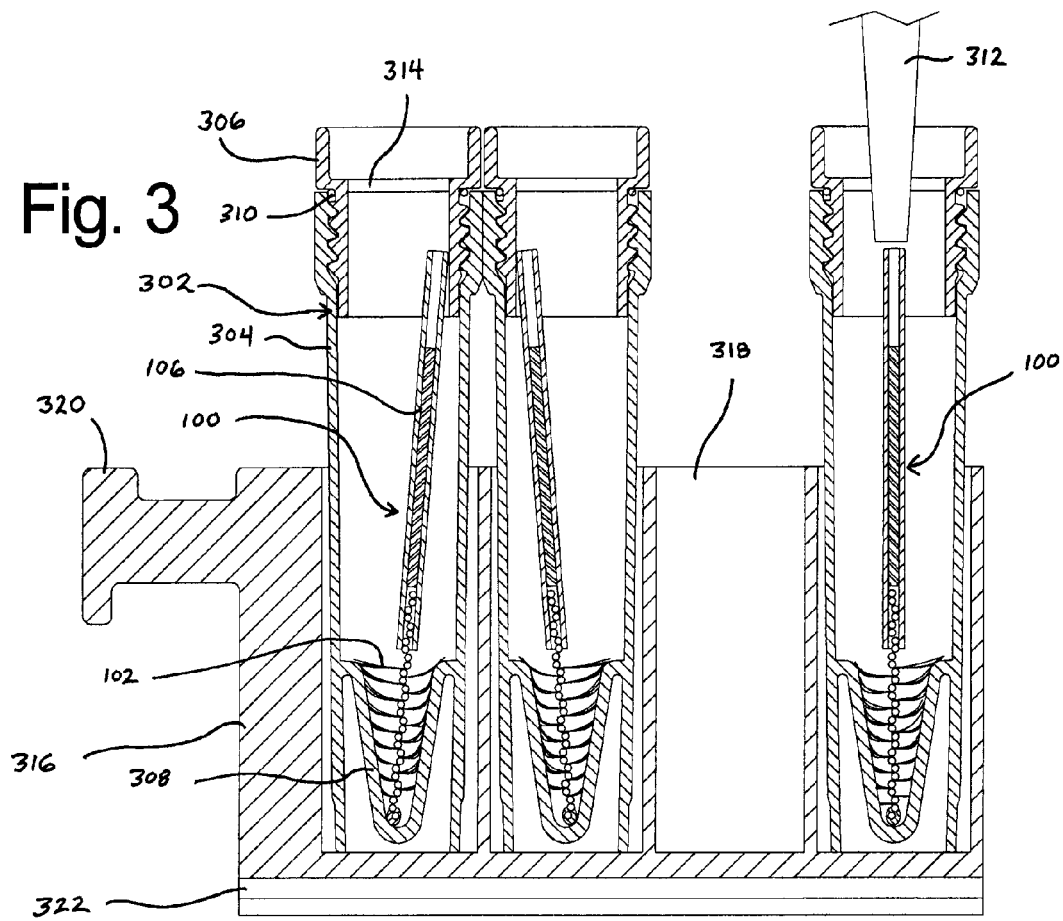
FIG. 3 is a cross-sectional side view of a first exemplary embodiment of a sample rack having a number of collection tubes contained therein.

FIG. 3 illustrates an exemplary embodiment of collection tubes 302 containing sample carriers 100 such as the one described with respect to FIG. 1. Each tube 302 may include a tube body 304 and a cap 306. The tube body 304 may be shaped with a conical end 308 that generally matches the bristle 104 shape and size, in which case the conical end 308 may tend to hold the sample collector 100 with the handle 106 generally aligned with the center of the tube 302. Of course, other shapes for the tube 302 and sample collector 100 may result in the handle 106 being oriented along the tube axis. Other embodiments may have any other suitable geometry, regardless of whether that geometry tends to cause the handle 106 to orient along the axis of the tube 302. The cap 306 is threaded, snapped, or otherwise affixed to the end of the tube 302. For example, the cap 306 and tube 302 may have matching single-lead or multiple-lead threads. If necessary, a separate o-ring 310 or other type of seal may be used to seal the collection tube 302 when the cap 306 is installed. The cap 306 may have an openable top that allows a manually-operated or automated robotic pipette 312 (or other devices) to enter the tube 302. For example, the cap 306 may have a pierceable membrane 314 that is penetrated before or when the pipette 312 is lowered into the tube 302. Of course, in other embodiments, the cap 306 may simply be removed before the pipette 312 is lowered into the tube 302. The tube 302 and cap 306 may be made of any suitable material, as known in the art.

Figure 4:
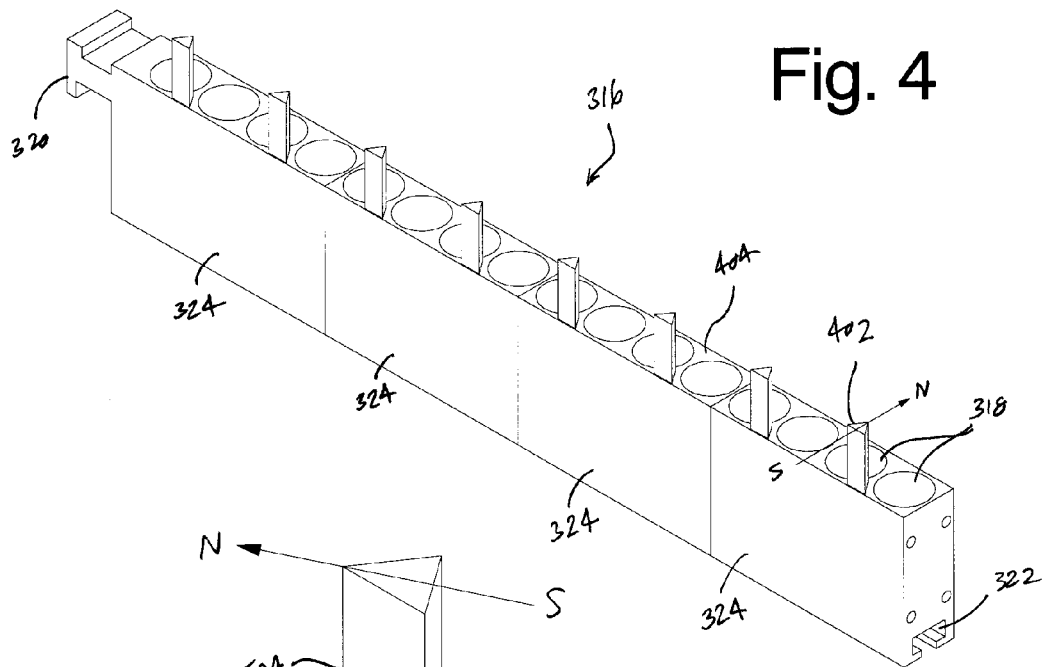
FIG. 4 is an isometric view of the embodiment of FIG. 3, showing additional exemplary features thereof.

Referring now to FIGS. 3 and 4, the tubes 302 may be held in a sample rack 316 having sockets 318 into which the tubes 302 fit. If desired, the sockets 318 may be adapted to receive and hold collection tubes having a variety of shapes and sizes. In the illustrated example, the rack 316 has four sockets 318, three of which are shown occupied. The rack 316 may be shaped and configured in any suitable way to facilitate its use in an automated sampling system. For example, the rack 316 may have a handle 320 at one end, and a track 322 at the lower end that integrates into a corresponding track on a sampling machine (not shown). The rack 316 may include multiple segments 324 that are attached end-to-end to extend the length of the rack 316 to increase its sample-holding capacity. These segments 324 may be connected in any suitable way, as known in the art. The rack 316 also may contain as few as one socket, or any number up to 16 or even 30 or more sockets.

As shown in FIG. 3, and specifically to the rightmost tube 302 shown in the rack 316, it has been found that a pipette 312 can contact the sample carrier handle 106 as it is lowered into the tube 302 (a single pipette 312 is shown in FIG. 3, but it will be understood that multiple pipettes 312 may be simultaneously introduced into multiple tubes 302). This is particularly true with sample carriers 100 and tubes 302 that have matching shapes that tend to hold the sample carrier 100 vertically within the tube 302, but it is also a problem even when no such features are provided. In order to provide more certainty regarding the relative positions of the pipette 312 and the handles 106 during the aspiration process, one or more magnets may be provided to magnetically pull the handles 106 towards a predetermined location at or near the side of each tube 302, such as shown in the two tubes 302 at the left end of the rack in FIG. 3. In this position, the handles 106 are oriented off the center axis of the tube, such that they are unlikely to substantially interfere with the pipettes 312 as they are lowered generally along the tube's center axis and alongside of the sample collector 100 in order to aspirate the sample. If desired, the likelihood of collision with the handles may be even further reduced by repositioning the pipettes 312 at a location off the tube center axis and opposite the location of the handles 106. While the foregoing measure of using magnets to reorient the handles is expected to provide significant benefits to advance the art of automated pipette aspiration, it will be appreciated that some degree of error and occasional collisions between the pipette and the handle may still occur, but the frequency of such incidents is expected to be a greatly reduced.

It will be appreciated that the magnet or magnets may be provided before or during the aspiration process (that is, before or at the time the pipette 312 is lowered into the tube 302), and the number, location and operation of the magnets may be modified in any number of ways. For example, a single large magnet can be used to attract all of the handles 100 at once, one or more magnets may be provided for each tube 302, or magnets may be provided that move the handles 100 in some, but not all, of the tubes 302 in a given rack 316. Furthermore, the magnet or magnets may be mounted on the rack 316, on a part that is separate from the rack 316, on the tubes 312, on an extension that moves on conjunction with the pipette 312, or at any other suitable location that provides the desired magnetic force at the appropriate time. Any suitable configuration of magnets or magnets may be used, provided it or they have sufficient strength at the relevant distance to move the sample carrier handles out of the path of the pipettes (or other devices, if desired) that are inserted into the tube.

The term "magnet" is used herein to encompass permanent magnets, temporary magnets, electromagnets, and any other kind of magnetic field-generating device or object. Any suitable magnet may be used to move the handles 106. For example, one preferred magnet may be a rare-earth magnet such as a Neodymium magnet (also known at NDFeB, NIB or Neo magnets), which may have a chemical composition of $Nd_2Fe_{14}B$. Other permanent magnets may include samarium-cobalt magnets, Alnico magnets, ceramic magnets and ferrite magnets. An exemplary temporary magnet may comprise one or more steel rods that are located adjacent the tubes 302 and temporarily magnetized at the appropriate time by placing them in the field of one or more permanent magnets or electromagnets.

In the exemplary embodiment of FIGS. 3 and 4, the rack 316 includes permanent magnets 402 that are used to magnetically pull the sample carrier handles 106 towards the sides of the tubes 302. In this embodiment, one magnet 402 is provided for every two tubes. Each magnet 402 is next to, and may be partially between, two adjacent sockets 318. The magnets 402 also may be positioned at approximately the height of the magnetic insert 116 (if one is used) to apply the greatest attractive force to the handle 106. This location may be above the upper surface 404 of the rack 316, as shown, or at the surface level or below, as needed for the particular application. In the shown configuration, each magnet 402 substantially pulls only on the sample carrier handles 106 in the two adjacent sockets 318, and does not exert sufficient magnetic force to significantly attract any other sample carrier handles 100 located in other sockets 318 along the rack 316 (or at least not enough force to attract the other handles 100 over the influence of magnets 402 located adjacent those handles 100). The magnets 402 may be secured to the rack 316 using any suitable method or means. For example, the magnets 402 may be adhered to the rack 316 using glue or epoxy, molded in place in the rack 316, secured by friction fit into holes in the rack, connected to a metal plate on the rack 316 by magnetic attraction, and so on. In addition, the magnets 402 may be installed during the time the rack is manufactured, or added manually later as needed or desired.

In some cases, such as where the magnets 402 are closely spaced, it may be desirable to position and orient the magnets 402 so that their magnetic fields do not interfere with one another in such a way that forces to move the handles 106 are negated or reduced enough that one or more handles 106 fail to move in the desired manner. In doing so, consideration may be given to any effects the environment may have on the magnetic fields as the rack is positioned in an automated machine for the aspiration process. For example, the rack 316 may be located adjacent one or more similar or identical racks during aspiration, in which case the combined effects of the magnets in the adjacent rack or racks may be considered to ensure that the handles are properly moved during aspiration. Still further, the magnetic force of the magnets 402 may cause other conditions, such as attraction to parts located inside or near the automated machine, and attraction to adjacent racks. While these forces may be inconsequential, in some cases it may be desirable to reduce them by modifying the number. location and orientation of the magnets. Of course, where some benefit can be derived from amplifying these forces, that may be done as well.

Figure 5:
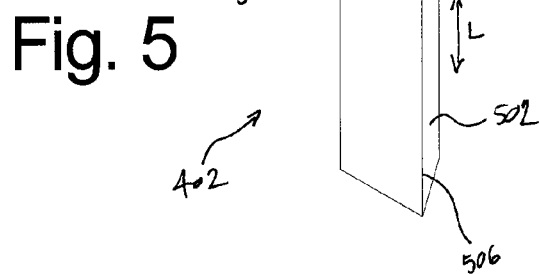
FIG. 5 is an isometric view of an exemplary embodiment of a magnet that may be used in the embodiment of a rack shown in FIG. 4 or in other embodiments.

The embodiment of FIG. 4 illustrates one exemplary arrangement of magnets 402 that is intended to reduce magnetic field interference between nearby magnets that might prevent the brushes from moving properly, and reduce the tendency of adjacent racks to attract to one another. In this embodiment, the magnets 402 comprise prism-shaped bars having an equilateral triangular cross section, as shown in more detail in FIG. 5. Each magnet 402 has a magnetic field that is oriented generally perpendicular to the length L of the magnet 402, and perpendicular to one surface 502 of the magnet. The south end of the field is at the surface 502, and the north end is at the edge 504 opposite the surface 502. In other embodiments, other pole orientations may be used. For example, the field may lie in parallel with one plane of the triangular cross section so that one edge 504 of the plane is the "north" edge, and the other edge 506 of the plane is the "south" edge. For ease of assembly, the magnetic field may be marked, such as by marking one of the magnetic pole edges. In this exemplary embodiment, the magnet 402 may comprise grade 50 NDFeB material, may have a length L of about 24 mm (about 0.96 inch), and each face may have a face width of about 6.35 mm (¼ inch). Of course, other materials and dimensions may be used in other embodiments. For example, the magnets 402 may be about 10 to 30 mm long, and have a face width of about 4 to 10 mm. Each magnet 402 may be oriented on the rack 316 with the "north" edge 504 pointing between the two adjacent sockets 318 and the south surface 505 facing away from the rack 316, as shown in FIG. 4. This arrangement is believed to mitigate both inter-field interference and the tendency for adjacent racks to adhere to one another by magnetic force, but other arrangements may be used in alternative embodiments, and it is expected that virtually any orientation will work, at least to some degree, in other embodiments.

Figure 6:
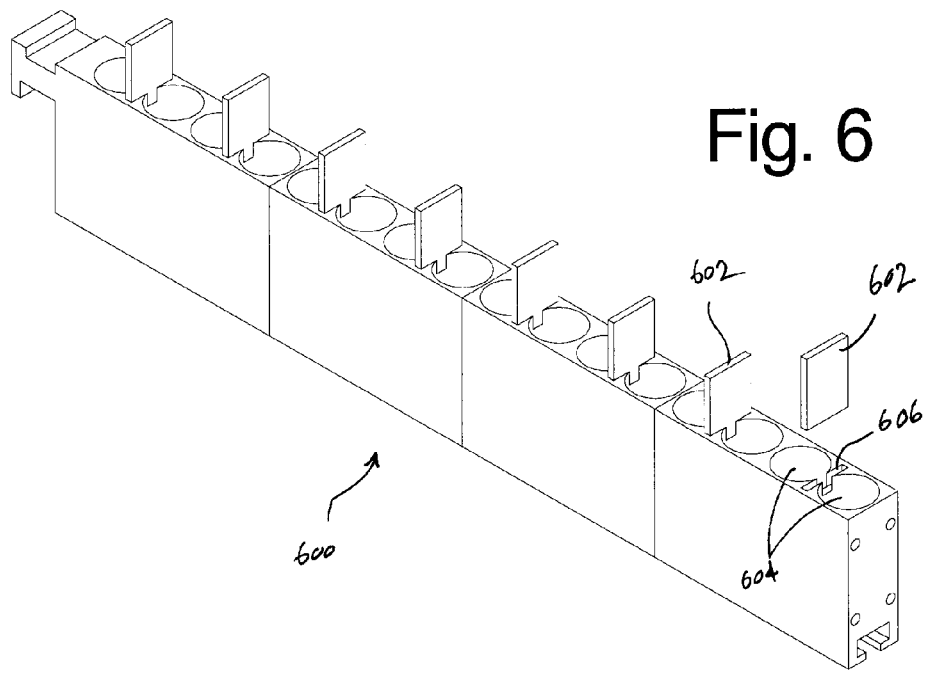
FIG. 6 is an isometric view of another embodiment of a sample rack.

Referring now to FIG. 6, another embodiment of a rack 600 having magnets 602 is illustrated. In this exemplary embodiment, the rack 600 has a series of sockets 604 positioned generally in a line along the rack 600 and adapted to receive collection tubes. A plate magnet 602 is positioned between each adjacent pair of sockets 604. Each magnet 602 may be installed in a slot 606, as shown by the rightmost magnet 602 which is not yet installed or has been removed. If desired, the slots 606 may be open to the adjacent sockets 604. As with other embodiments, the plate magnet 602 may have any suitable construction, including specific dimensions, material, grade, and pole orientation, as will be appreciated by persons of ordinary skill in the art without undue experimentation.

Figure 7:
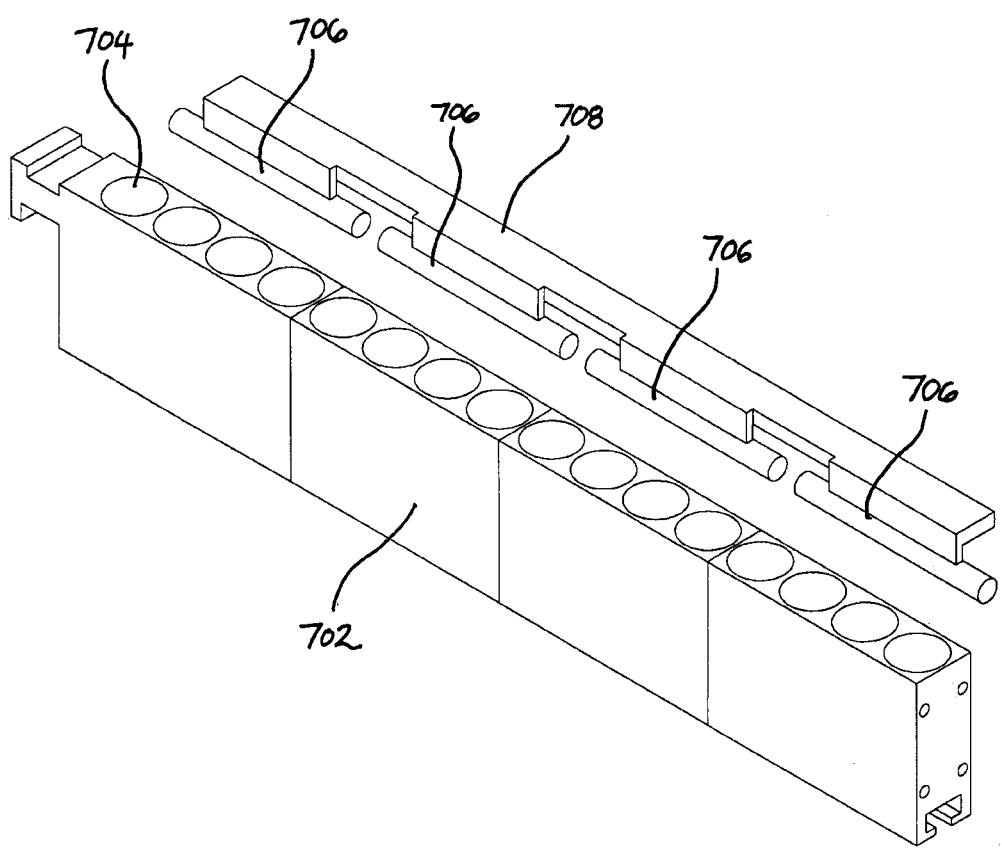
FIG. 7 is an isometric view of another embodiment of a sample rack and a separate magnet-holding platform.

Another embodiment is illustrated in FIG. 7. Here, a rack 702 having sockets 704 for receiving collection tubes is provided, and a number of magnets 706 are mounted on a separate platform 708. During processing, the magnets 706 may be moved into a suitable position to reorient sample collectors carried within the collection tubes at the appropriate time. This may be done, for example, by moving the platform 708 in unison with pipettes as they move into place to aspirate samples from the collection tubes. As another example, the platform 708 may be fixed in position adjacent a sample aspirating station within the machine, and as the rack 702 is moved next to the platform 708 to begin the aspiration process, the magnets 706 perform the desired reorientation of the sample collectors. Other variations and embodiments will be readily apparent to persons of ordinary skill in the art in view of the present disclosure.

As will be apparent from the foregoing description of exemplary embodiments, a sampling system including sample collectors having magnetic handles (or magnetic upper portions) and a corresponding magnet or magnets to move the sample collectors at the appropriate time, can be used in various ways in a sampling process. For example, in one relatively simple embodiment, samples are processed by acquiring a sample with a sample collector, placing the sample collector in a collection tube, moving the sample collector within the sample tube using a magnetic force, and inserting a testing tool into the collection tube. In the medical context, the sample acquisition steps (the first two) are likely to be done by a clinical doctor or nurse, and the remaining steps are likely to be conducted by a testing lab, but all of the steps may be conducted by the same individual, facility or entity. It is believed that the use of magnetic handles, such as described herein, will facilitate the use of automated systems to aspirate samples directly from a collection tube having a collection brush still in the tube, without significant risk that the pipette tip will strike the handle.

Figure 8:
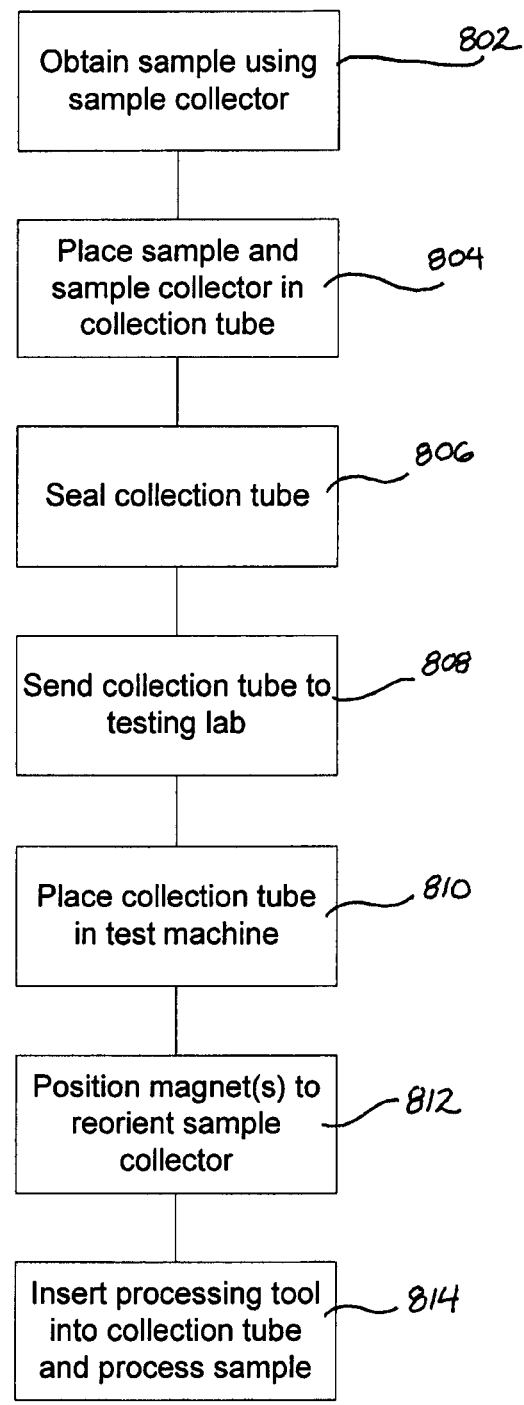
FIG. 8 is a schematic flow diagram illustrating one exemplary embodiment of a process for collecting and testing a sample.

Many variations and arrangements of the foregoing process can be made. For example, one embodiment of a test process is shown in FIG. 8. In this embodiment, the system is used to test for the presence of Human Papilloma Virus genetic material in a cervical sample, but other uses are possible. In a first step 802, a sample collector in the form a cervical brush is used to collect a sample from a patient. In the second step 804, the sample and sample collector are placed in a collection tube. As noted above, the sample collector may be broken at a score line so that only the brush portion and part of the handle are installed in the collection tube. Also as explained above, at least part of the sample collector, preferably the handle, is magnetic. At step 806, the collection tube is sealed by a cap and at step 808 it is delivered to a testing lab. The testing lab places the unopened collection tube into a testing machine in step 810. The tube may be installed in a rack before being placed in the machine, as described above, but the use of a separate rack is exemplary and not required of all embodiments of the methods, apparatus and systems described herein. Next, in step 812, one or more magnets are positioned next to the collection tube. As part of this step, the magnets pull on a magnetized portion of the sample collector to move at least a portion of the sample collector to a new location within the collection tube (or hold the sample collector in place if it is already at the desired location). As explained above, step 812 may be conducted at the time the collection tube is placed in a rack, which may occur before the rack is placed in the machine. As such, step 812 may occur before step 810. Next, in step 814, a device, such as an aspirating pipette, is inserted into the collection tube to process or remove some or all of the sample. The device preferably is moved by an automated robotic arm, but this is not required. Of course, numerous variations on the foregoing process are possible, such as reordering steps, conduction only portions of the process, and adding additional steps.

While numerous other benefits of the various embodiments will be apparent from the foregoing disclosure, certain significant benefits are expected to be realized when using the disclosed methods and processes in HPV testing processes. For example, using the foregoing systems and methods, it is expected that an HPV testing apparatus can be automated to handle as many as 20 racks or more of collection tubes at a single time, and as many as 168 or more sample collection tubes can be aspirated at one time or in a single sequential process. Each aspiration may draw about 100 μL to about 2 mL from a collection tube containing, for example, about 100 μL to about 4 mL of liquid sample preservation media.

It should be understood that the foregoing embodiments are exemplary only, and other embodiments will be apparent to those of ordinary skill in the art in light of the teachings provided herein. For example, while the foregoing embodiments describe systems and methods for use in medical sampling procedures, it will be readily apparent that these may be modified for use in other processes. Other variations will be apparent to those of ordinary skill in the art in view of the present disclosure and with practice of the invention.

The invention claimed is:

1. An automated sample aspirating method comprising:
providing one or more collection tubes, each collection tube being oriented along a vertical axis and having a sample carrier located therein;
applying a magnetic force to move at least a top end of each sample carrier to a location off a vertical center axis of the respective collection tube;
inserting an aspirator, generally along the vertical axis, into the one or more collection tubes to a vertical position adjacent at least a portion of the respective sample carrier; and
aspirating a fluid from the one or more collection tubes through the aspirator; and
wherein each sample carrier comprises a handle and a tapered tip, and each collection tube comprises a tapered lower end configured to hold each respective sample carrier with its handle generally along the vertical center axis until the magnetic force is applied.

2. The automated sample processing method of claim 1, wherein each sample carrier comprises a handle and a tip, the tip being provided on the handle by a metal wire.

3. The automated sample processing method of claim 2, wherein applying a magnetic force to move at least a top end of each sample carrier to a location off a vertical center axis of the respective collection tube comprises applying a magnetic force to the metal wire of each sample carrier.

4. The automated sample processing method of claim 1, wherein each collection tube comprises a cap, and the step of inserting the aspirator comprises piercing the cap with the aspirator.

5. The automated sample processing method of claim 1, wherein each collection tube comprises a cap, the cap being dimensioned to permit an adjacent portion of the sample carrier to move laterally across the sample tube.

6. The automated sample processing method of claim 1, wherein providing one or more collection tubes comprises providing a plurality of collection tubes in a rack.

7. The automated sample processing method of claim 6, wherein providing the plurality of collection tubes in the rack comprises providing each collection tube in a respective container location on the rack.

8. The automated sample processing method of claim 6, wherein applying a magnetic force to move at least a top end of each sample carrier to a location off a vertical center axis of the respective collection tube comprises providing one or more magnets in the rack.

9. The automated sample processing method of claim 8, wherein providing one or more magnets in the rack comprises providing a magnet between an adjacent pair of collection tubes.

10. The automated sample processing method of claim 8, wherein providing one or more magnets in the rack comprises providing a single magnet for each two collection tubes.

11. The automated sample processing method of claim 10, wherein at least one magnet comprises a first face adjacent a first collection tube, and a second face adjacent a second collection tube.

12. The automated sample processing method of claim 11, wherein the at least one magnet comprises a triangular magnet.

13. The automated sample processing method of claim 8, wherein:
providing the plurality of collection tubes in the rack comprises providing the plurality of collection tubes in a row extending along a linear centerline; and
providing one or more magnets in the rack comprises providing one or more magnets only on one side of the centerline.

14. An automated sample aspirating method comprising:
providing one or more collection tubes, each collection tube being oriented along a vertical axis and having a sample carrier located therein, each sample carrier comprising a handle and a tip provided on the handle by a metal wire;

applying a magnetic force to move at least a top end of each sample carrier to a location off a vertical center axis of the respective collection tube;

inserting an aspirator, generally along the vertical axis, into the one or more collection tubes to a vertical position adjacent at least a portion of the respective sample carrier; and aspirating a fluid from the one or more collection tubes through the aspirator; and wherein each sample carrier tip comprises a tapered tip, and each collection tube comprises a tapered lower end configured to receive each respective sample carrier's tapered tip to hold each respective sample carrier with its handle generally along the vertical center axis until the magnetic force is applied.

15. The automated sample processing method of claim 14, wherein applying a magnetic force to move at least a top end of each sample carrier to a location off a vertical center axis of the respective collection tube comprises applying a magnetic force to the metal wire of each sample carrier.

16. The automated sample processing method of claim 14, wherein each collection tube comprises a cap, and the step of inserting the aspirator comprises piercing the cap with the aspirator.

17. The automated sample processing method of claim 14, wherein providing one or more collection tubes comprises providing a plurality of collection tubes in a rack.

18. The automated sample processing method of claim 17, wherein applying a magnetic force to move at least a top end of each sample carrier to a location off a vertical center axis of the respective collection tube comprises providing one or more magnets in the rack.

19. The automated sample processing method of claim 18, wherein providing one or more magnets in the rack comprises providing a magnet between an adjacent pair of collection tubes.

20. The automated sample processing method of claim 19, wherein at least one magnet comprises a first face adjacent a first collection tube, and a second face adjacent a second collection tube.

21. The automated sample processing method of claim 20, wherein the at least one magnet comprises a triangular magnet.

22. An automated sample aspirating method comprising:
providing one or more collection tubes, each collection tube having a cap and each collection tube being oriented along a vertical axis and having a sample carrier located therein;

applying a magnetic force to move at least a top end of each sample carrier to a location off a vertical center axis of the respective collection tube;

piercing the cap with an aspirator and inserting the aspirator, generally along the vertical axis, into the one or more collection tubes to a vertical position adjacent at least a portion of the respective sample carrier; and aspirating a fluid from the one or more collection tubes through the aspirators and wherein each sample carrier comprises a handle and a tapered tip, and each collection tube comprises a tapered lower end configured to hold each respective sample carrier with its handle generally along the vertical center axis until the magnetic force is applied.

23. The automated sample processing method of claim 22, wherein each sample carrier comprises a handle and a tip, the tip being provided on the handle by a metal wire, and wherein applying a magnetic force to move at least a top end of each sample carrier to a location off a vertical center axis of the respective collection tube comprises applying a magnetic force to the metal wire of each sample carrier.

24. The automated sample processing method of claim 22, wherein providing one or more collection tubes comprises providing a plurality of collection tubes in a rack.

25. The automated sample processing method of claim 24, wherein applying a magnetic force to move at least a top end of each sample carrier to a location off a vertical center axis of the respective collection tube comprises providing one or more magnets in the rack.

26. The automated sample processing method of claim 25, wherein providing one or more magnets in the rack comprises providing a magnet between an adjacent pair of collection tubes.

27. The automated sample processing method of claim 26, wherein at least one magnet comprises a first face adjacent a first collection tube, and a second face adjacent a second collection tube.

28. The automated sample processing method of claim 27, wherein the at least one magnet comprises a triangular magnet.

* * * * *